(12) United States Patent
Raju

(10) Patent No.: US 11,666,466 B2
(45) Date of Patent: Jun. 6, 2023

(54) MODIFIED Z STENTS FOR ILIAC VEIN STENTING

(71) Applicant: Seshadri Raju, Jackson, MS (US)

(72) Inventor: Seshadri Raju, Jackson, MS (US)

(*) Notice: Subject to any disclaimer, the term of this patent is extended or adjusted under 35 U.S.C. 154(b) by 0 days.

(21) Appl. No.: 17/455,886

(22) Filed: Nov. 19, 2021

(65) Prior Publication Data

US 2022/0096252 A1 Mar. 31, 2022

Related U.S. Application Data

(63) Continuation-in-part of application No. PCT/US2020/033639, filed on May 19, 2020.

(60) Provisional application No. 62/850,249, filed on May 20, 2019.

(51) Int. Cl.
*A61F 2/89* (2013.01)
*A61F 2/852* (2013.01)

(52) U.S. Cl.
CPC ............... *A61F 2/852* (2013.01); *A61F 2/89* (2013.01); *A61F 2220/0075* (2013.01); *A61F 2220/0091* (2013.01); *A61F 2230/0013* (2013.01); *A61F 2230/0054* (2013.01); *A61F 2250/006* (2013.01)

(58) Field of Classification Search
CPC .... A61F 2/852; A61F 2/89; A61F 2220/0075; A61F 2220/0091; A61F 2230/0013; A61F 2230/0054; A61F 2250/006; A61F 2002/067; A61F 2002/828; A61F 2/07
USPC .................................. 623/1.15–1.16
See application file for complete search history.

(56) References Cited

U.S. PATENT DOCUMENTS

| | | | | |
|---|---|---|---|---|
| 5,282,824 | A * | 2/1994 | Gianturco | A61F 2/86 623/1.13 |
| 6,197,049 | B1 * | 3/2001 | Shaolian | A61F 2/90 623/1.35 |
| 7,942,921 | B2 * | 5/2011 | Nissl | A61F 2/915 606/198 |
| 8,192,482 | B2 * | 6/2012 | Goicoechea | A61F 2/954 623/1.16 |
| 8,795,350 | B2 | 8/2014 | Gillespie et al. | |
| 8,840,657 | B2 * | 9/2014 | Hartley | A61F 2/86 623/1.13 |
| 10,092,425 | B2 * | 10/2018 | Bogert | A61L 31/14 |
| 10,456,281 | B2 * | 10/2019 | Armstrong | A61F 2/89 |
| 10,758,381 | B2 * | 9/2020 | Longo | A61F 2/848 |
| 10,959,826 | B2 * | 3/2021 | Skender | A61F 2/07 |
| 11,406,517 | B2 * | 8/2022 | Guo | A61F 2/915 |
| 11,440,907 | B1 * | 9/2022 | Yu | C07D 403/04 |
| 2007/0289677 | A1 | 12/2007 | Ma et al. | |
| 2009/0259298 | A1 | 10/2009 | Mayberry et al. | |
| 2010/0030320 | A1 * | 2/2010 | Feller, III | A61F 2/966 623/1.11 |

(Continued)

OTHER PUBLICATIONS

PCT/US2020/033639—see the Written Opinion of the International Searching Authority (dated Sep. 18, 2020), International Search Report (dated Sep. 18, 2020).

*Primary Examiner* — Suzette J Gherbi
(74) *Attorney, Agent, or Firm* — Intellectual Property Consulting, LLC; Bernard F. Meroney

(57) ABSTRACT

The invention includes modifications of a Z stent to allow the top struts of two Z stents deployed in the vena cava in a bilateral relationship, to interleave. One embodiment includes Z stents with angled top surfaces. A second embodiment includes Z stents having an intermediary suture but lacking the top suture in the topmost stent of a stacked stent module.

14 Claims, 11 Drawing Sheets

(56) References Cited

U.S. PATENT DOCUMENTS

| | | | |
|---|---|---|---|
| 2010/0249902 A1* | 9/2010 | Sakai | A61F 2/89 623/1.18 |
| 2013/0289713 A1 | 10/2013 | Pearson et al. | |
| 2020/0390575 A1* | 12/2020 | Guo | A61F 2/915 |

* cited by examiner

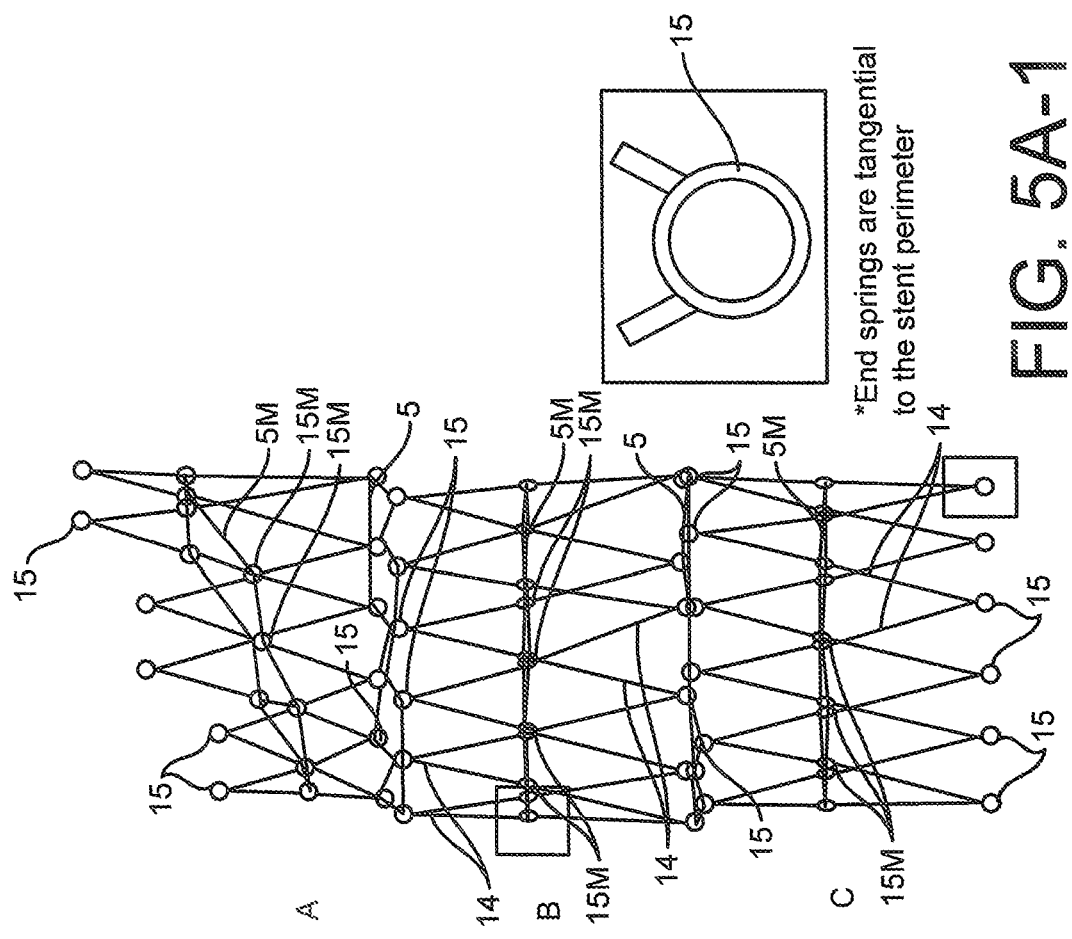
FIG. 5A
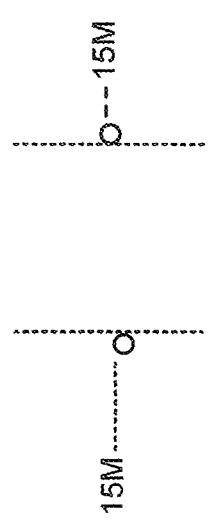
FIG. 5A-1
*End springs are tangential to the stent perimeter
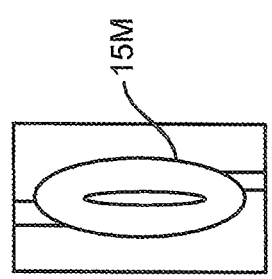
FIG. 5B
*Midline loops are perpendicular to the stent cylinder surface
FIG. 5B-1

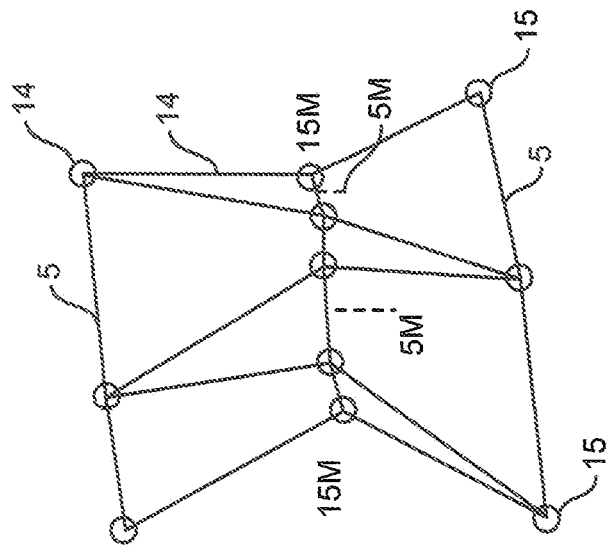
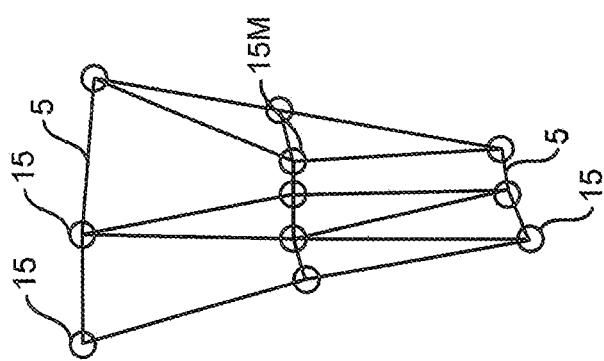
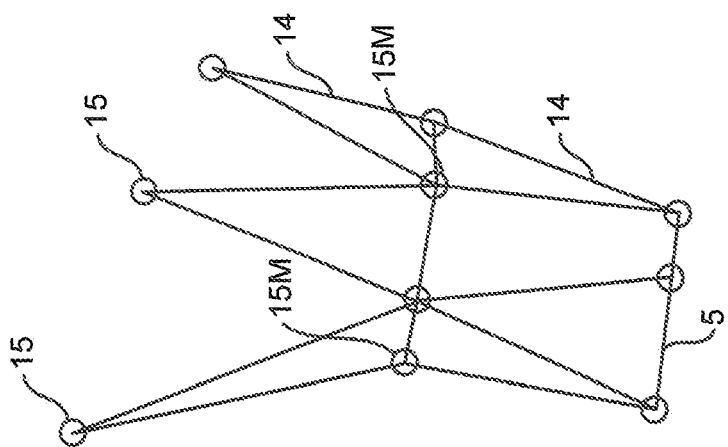
FIG. 6B
FIG. 6C
FIG. 6A

MODIFIED Z STENTS FOR ILIAC VEIN STENTING

PRIORITY CLAIM

This application is a continuation in part of PCT/US20/33639 filed May 19, 2020, which claimed the priority benefit of U.S. Provisional Patent Application No. 62/850,249 filed on May 20, 2019.

BACKGROUND OF THE INVENTION

The iliac vein presents unique circumstances for stenting, particularly in the common iliac. The upper end of the common iliac vein is seen as a "choke point" due to compression of the vein by the overlying artery. Stents in this area must be sufficiently stiff to resist collapse or partial compression, which results in decreased fluid flow through the stent. One stent found suitable for use in this area is the Z stent offered by Cook Medical, as originally described in U.S. Pat. No. 4,580,568 to Gianturco, incorporated by reference.

The original Z stent 1 as described involves a stainless steel or alloy wire device, where the wire is formed into a zigzag pattern into a closed cylinder. The two open ends of the wire forming the stent are joined (for instance, by welding) to form a closed cylinder, where the cylinder walls are formed by wire struts 14, where two adjacent struts (half of a Z) form a V shape with large openings between the legs of the struts. See FIG. 1. This results in a repeating pattern of "Z" or V shapes around the cylinder, where the Zs are orientated along the lumen axis. See FIG. 1. Each terminating end of a strut (top and bottom) may terminate in a small loop or eye 15, such as shown in FIG. 1. If the loops can be formed directly from bending the wire during zig-zag formation, the loops 15 can form a spring or a basing loop.

The strength of the Z stent can be modified by changing the diameter of the selected wire, the material forming the wire, and the number of "Zs" contained in the stent. The Z stent can be compressed into a collapsed flattened (non-deployed) state by applying an inward force around the entire perimeter of the stent, and the stent flattens in a direction perpendicular to the cylindrical axis of the stent. See FIG. 1B. The deployed stent, however, generally resists collapse from an inward force applied only partially around the stent perimeter, such as exerted by the overlying artery at the choke point in the common iliac.

The Z stent can be lengthened or shortened by modifying the length of the struts. The original Z stent was encased in a sheath and had six "Vs" or 12 struts, with six terminating end loops on the top end of the stent, and another six loops on the bottom end of the stent. See FIG. 1 (sheath excluded). The Z stents became popular, with many variations. One variation was to join two or more Z stents together into a stent module by stacking one on top of the other and joining the stacked stents using a suture or wire 5 threaded through the eyes or loop 15 of the two stents at the join (the bottom loops of the topmost stent and the top loops of the adjacent stacked stent). Two or more Z stents can be stacked into a longer stent module by such a process. See FIG. 2. Stacked cylinders Z stents are joined together by a suture-like structure formed of plastic (such as nylon) or nitinol or stainless wire materials (all considered as "sutures") where the suture passes through adjacent loops or eyes (either considered a "loop" for purposes herein) at the top of the lower Z stent and the bottom upper adjacent Z stent of the adjacent stacked cylinders. See FIG. 2. Additionally, a similar strong suture, such as nylon or other plastic, or nitinol or stainless steel wire 5 would be threaded through the uppermost cylinder terminating loops, and another 5 through the bottommost cylinders terminating bottom loops, to prevent the top and bottom struts from opening or splaying open. See U.S. Pat. Nos. 5,282,824 and 5,507,771 also issued to Gianturco, incorporated by reference. The typical sheath 90 surrounding the stent cylinder is also shown in FIG. 2. The terminating loops 15 of the top or bottom cylinders may be plated, for instance with gold, to provide radiographic visualization during placement. By stacking cylindrical stents, a long stent comodule can be made with some flexibility between the two (or more) stacked cylinder stents, helping in placement and delivery in a twisted environment.

Additionally, other materials have been used, such as nitinol. The Z stent has been also adapted for fenestrated stents. See WO 2005/034808 and U.S. Pat. No. 8,545,549; and with modifications to the "Z" structure, see for instance U.S. Pat. No. 6,270,524, (all incorporated by reference) where each "Z" band is stacked or connected to adjacent Z bands with a Z member that has an upper or lower extension to the interior Z structure that ties to an upper or lower Z band. See also U.S. Pat. Nos. 8,012,196 and 5,443,498 where bands of Z shaped struts are coupled to bands of S shaped struts, or U.S. Pat. No. 5,443,498, where the Z bands have been replaced with looped bands. All of the above will be considered Z stents and incorporated by reference. All of the above demonstrate the desired resistance to compression of the Z stent, with large sidewall openings between stent struts.

As mentioned above, a stenosis is often present in the common iliac at the choke point. This stenosis can often be congenital in origin. In post-thrombotic cases, this choke point is the site of increased post-thrombotic fibrosis due to incomplete resolution of the thrombus. A stent with strong radial strength is required at this site, such as is present in a Z stent. The stenotic lesion often extends a variable length into the vena cava where the opposite common iliac vein confluences. In this case, extension of the stent into the vena cava is desirable to cover the stenosis in its entirety. However, this extension presents difficulties for stent deployment, as too much extension can "jail" the opposite common iliac vein, impeding flow through it. This can result in deep venous thrombosis in that extremity. Too little extension can result in incomplete coverage of the lesion. The vena cava extension thus poses difficulties in single stage or sequential bilateral stent deployment.

Some mechanism for "meshing" or interdigitating of the Z stent struts at the upper end of the bilateral stents extending into the vena cava is needed. This meshing of both is desirable to reduce the overall apparent size of the two stents in the inferior vena cava to conform to the size of the inferior vena cava, thus decreasing the potential for jailing. The Z stent design commonly used in the common iliac has nylon sutures 5 at the upper and lower ends of a single cylinder or stacked cylinders. These sutures prevent meshing of bilateral stents in the vena cava. Bilateral stents of this design may have a side-by-side maximum diameter much larger than the inferior vena cava, an undesirable result.

SUMMARY OF THE INVENTION

The invention includes modifications of a Z stent to allow the top struts of two Z stents deployed in the vena cava in a bilateral relationship to interleave. One embodiment includes Z stents with angled top surfaces. A second embodiment includes Z stents having an intermediary suture but lacking the top suture, in the topmost stent of a stacked stent module.

BRIEF DESCRIPTION OF THE DRAWINGS

FIG. 5A is a side view of three stacked Z stents where the topmost stent has a top portion that is formed at an angle.

FIG. 5A-1 is a front view of the top or bottom loop, with is formed in the surface of the stent cylinder (tangential to the stent perimeter).

FIG. 5B is a front elevation detailed view of one embodiment of an intermediary loop.

FIG. 5B-1 is a cross section through the stent cylinder showing the intermediary loop extending away from the cylinder.

FIG. 6A is a front elevation view of a single Z stent deployed with intermediary loops positioned on ach strut in an intermediary loops position between top loops and bottom loops with an associated suture 6M but no top suture present. Or a longer top suture used (shown).

FIG. 6B is a side elevation view of a deployed Z stent with intermediary loops, and top, bottom, and intermediary sutures, where the top and bottom sutures are substantially equal in length and the intermediary suture is shorter in length.

FIG. 6C is a side elevation view of a deployed z stent with intermediary loops where the bottom suture is shorter than the intermediary suture in length, and the intermediary suture is shorter in length than the top suture.

DETAILED DESCRIPTION OF THE PREFERRED EMBODIMENTS OF THE INVENTION

Figure 3A:
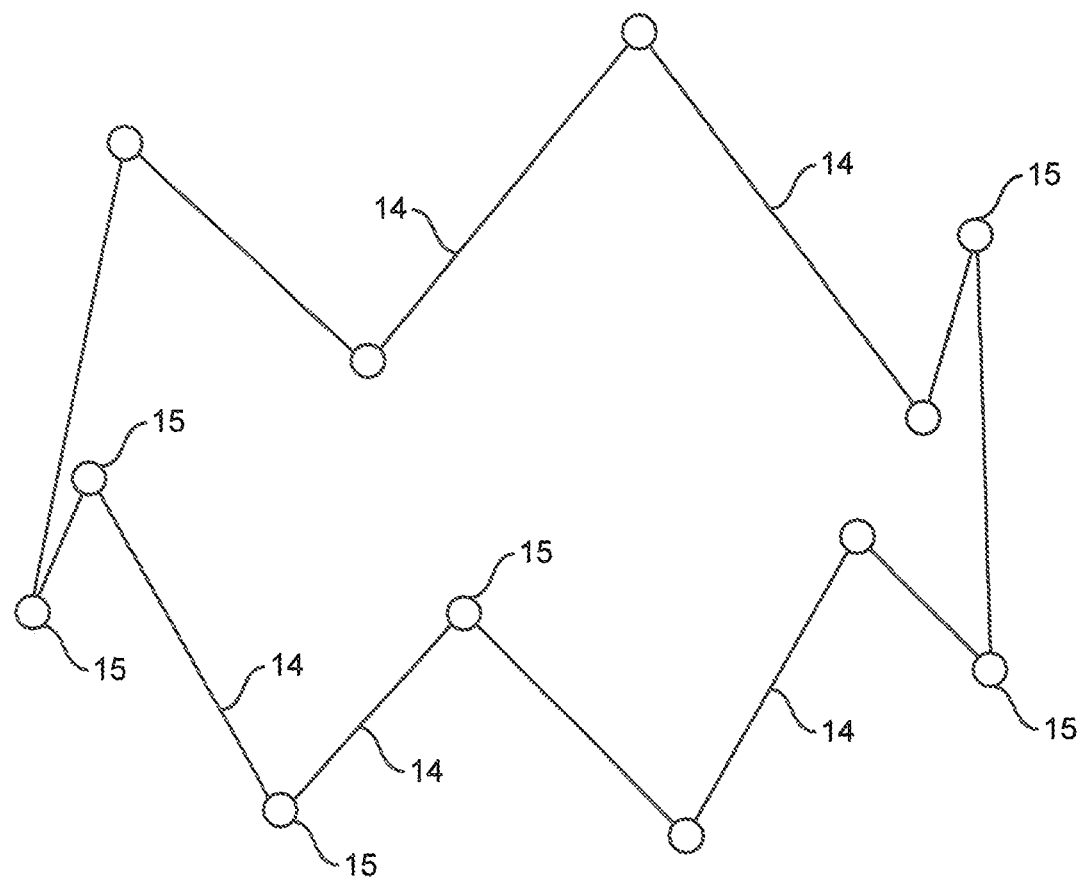
FIG. 3A shows a front perspective review of single Z stent fully unsprung.
Figure 3B:
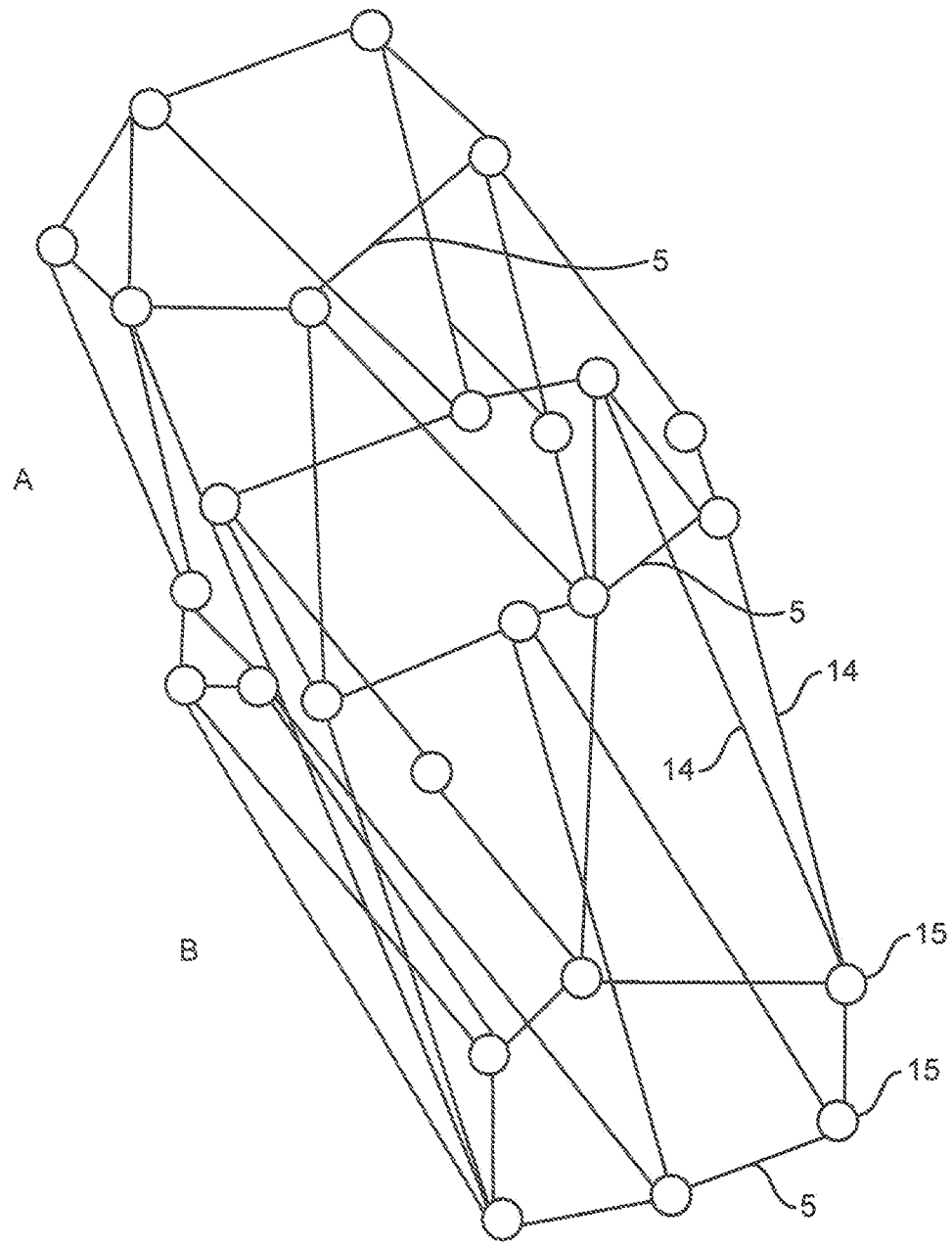
FIG. 3B is a front prospective view of two stacked Z stents in the fully deployed state.
Figure 4:
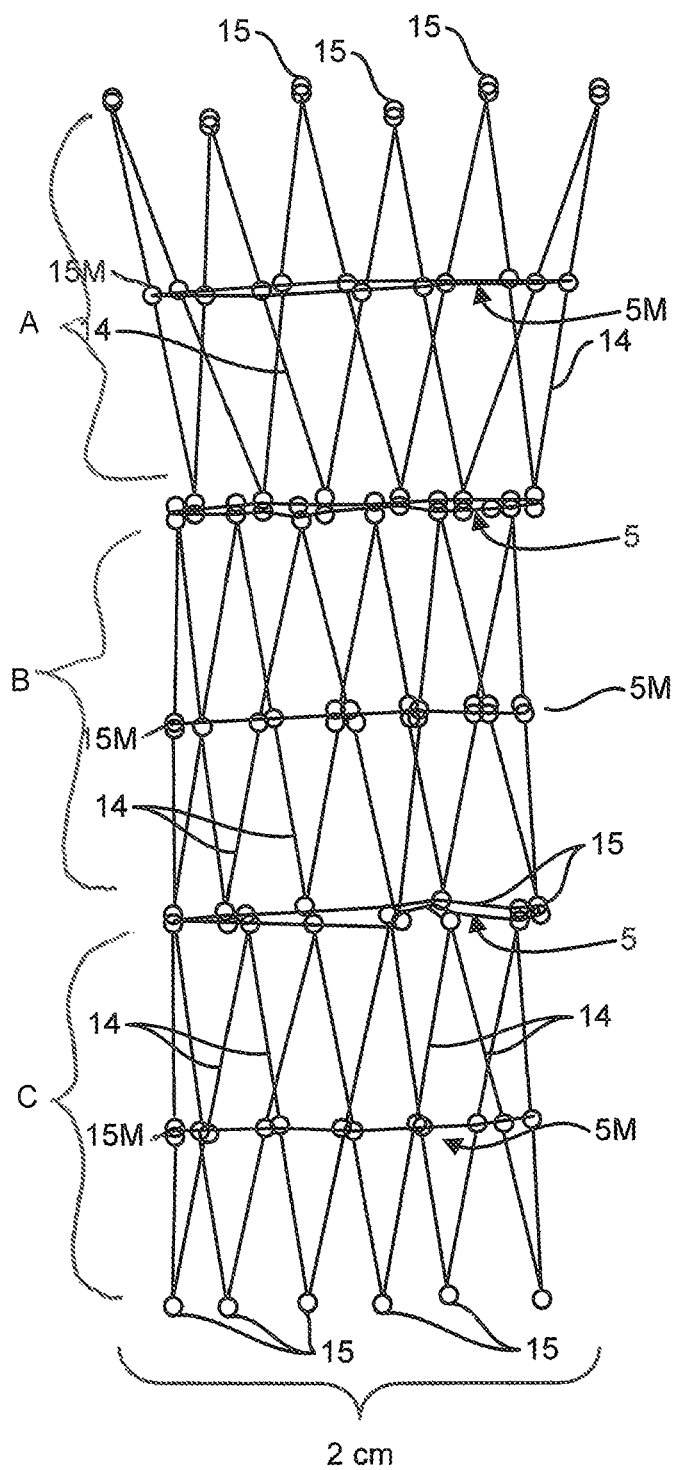
FIG. 4 is a side elevation view of three stacked Z stents having additional loops placed on each strut at an intermediary point between the top and bottom of each associated stent.

The traditional two stacked Z stents used in the common iliac includes two stacked cylinders and three circumferential ties (such as nylon) or sutures, one at each terminating end 5 of the module and one 20 at the junction of the two cylinders. All considered sutures, and all sutures are closed, that is, forming a closed loop. The completely "unsprung" Z stent (i.e., not restrained by a suture) for use in the vena cava is about 4-5 cm in diameter. See FIG. 3A. These stents are spring loaded when deployed by inclusion of the sutures 5 and 20, as the suture restrains the expansion of the Z stent and prevents the deployed stent from transitioning to the totally unsprung state. Typically, the deployed state of a single Z stent for the iliac vein will have a diameter of 2.5 cm, and a comparable length. The deployed diameter is determined by the length of the sutures or ties. See FIG. 3B. The suture is sized to permit stent expansion to the approximate size of the healthy vein (lacking lesions) into which it will be deployed, which is a smaller diameter than the unsprung stent shown in FIG. 3A. For instance, in the common iliac deployment, the deployed stent may expand to a diameter of about 2.5 cm, with each Z stent cylinder having a comparable length (2.5 cm). Consequently, the Z stents provide baseline hoop strength in a tangential direction to the stent perimeter (as the spring-loaded biasing loops 15 through which the suture 5 pass are preferably formed flat with the cylinder perimeter of the stent). See FIG. 5B-1. Additional radial strength arises from the tension present in the incomplete deployment of the cylinders caused by the restriction of the sutures or ties. Several modifications of the Z stent designs are proposed to help Z stents to mesh or interdigitate in the join at the topmost end within the vena cava. The modifications are described with respect to a two or three stack Z stent module, but similar modifications can be made with two or more stacked modified Z stents, or even a single Z stent.

Three Cylinders

The preferred basic stent module will have three stacked Z stent cylinders A, B and C, each 2.5 cm long. This will increase the length from the current two stacked stents from 5 cm to 7.5 cm. This will reduce the chances of migration and minimize the number of stents used to cover the relatively long segment length in the common and external iliac veins. Exterior facing barbs 60 present in some Z stent designs can be removed. However, a single or two stacked stents may also be used, in which case the barbs 60 may remain to resist migration.

First Embodiment—Intermediary Waist Suture

Figure 1:
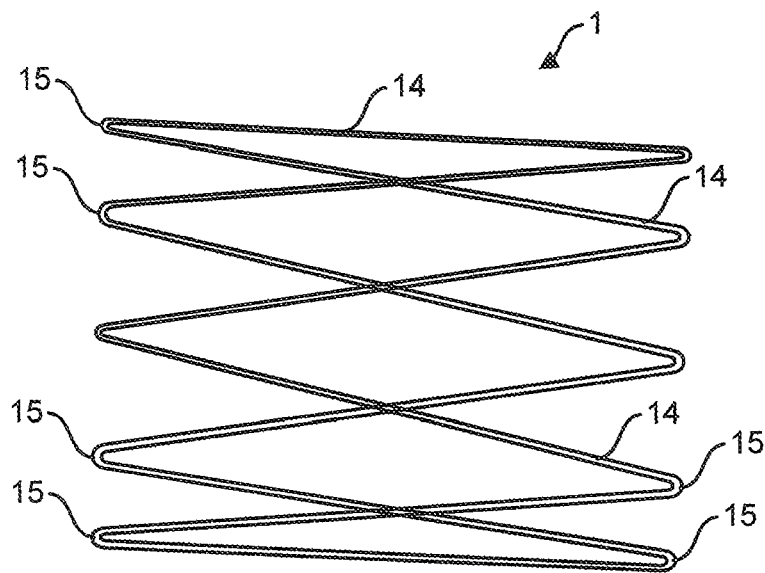
FIG. 1 is a side elevation view of a prior art Z stent with sutures removed.
Figure 1A:
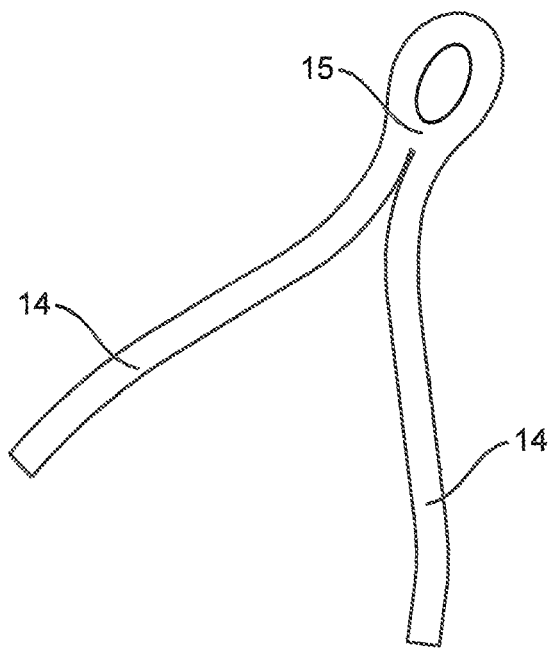
FIG. 1A is a detail top view of the terminating end of a strut, showing one embodiment of an eyelet or loop.
Figure 1B:
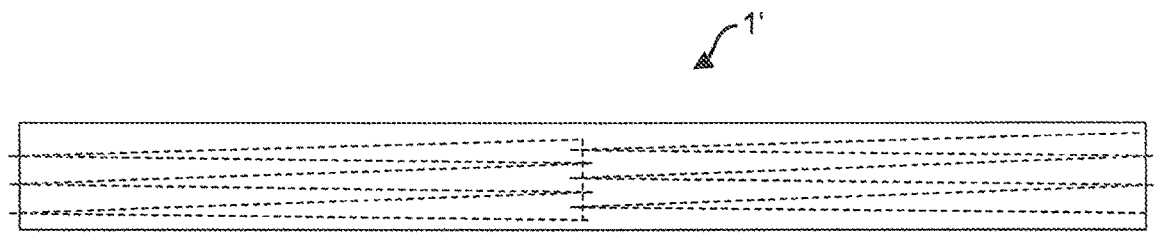
FIG. 1B is a side view of a fully compressed Z stent.
Figure 2:
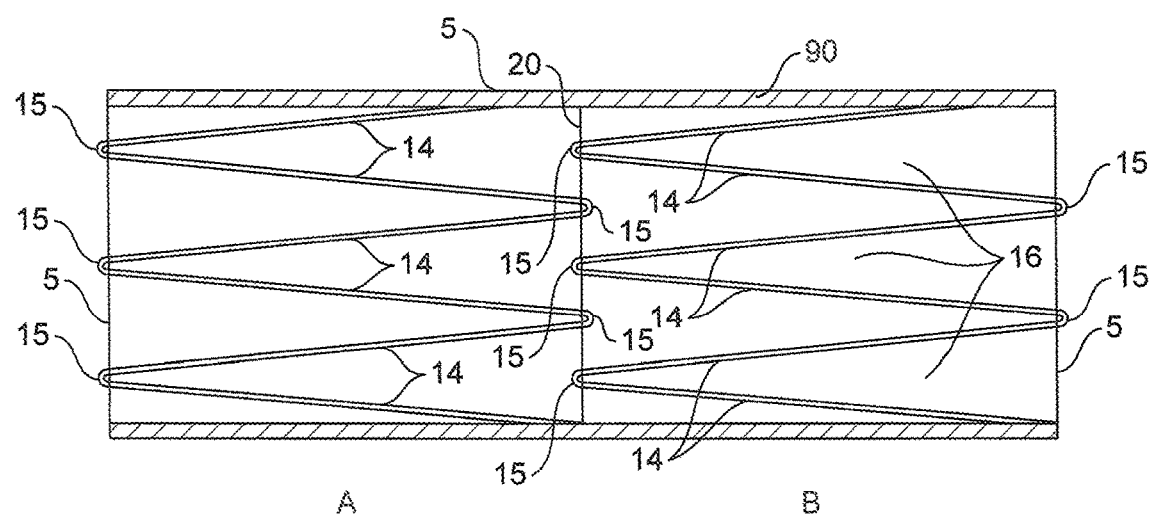
FIG. 2 is a side elevation view of two stacked Z stents joined together by a suture at the overlap.

An intermediary waist suture 5M (a suture placed on each strut of the topmost Z stent cylinder at a point between the top and bottom of the struts (preferably positioned at a point where the intermediary waist stent 5M will extend into the vena cava). For a stent of length 2.5 cm, "midline sutures" are provided, positioned at about 1.25 cm from the top of the stent module or about halfway down the wall of lengths of the struts in the topmost stent. Such an intermediary suture is preferably placed in the uppermost stent, more preferably the upper and lower or bottom cylinder stents and most preferably in each strut of each cylinder in the stacked stent module. A suture 5 is also provided between each stacked cylinder to join the cylinders through the overlapping loops into a single integrated Z stent module. The upper cylinder A's topmost suture 5 and optionally the lowermost cylinder's' bottommost sutures 5 in stent cylinder C, used in the prior art three-cylinder (or two-cylinder) Z stent module, are eliminated in the proposed modification. See FIG. 5A. To provide for the intermediary suture 5M, the wires forming the struts of the stent can be used to create an intermediary loop 15M, such as on the midline of each strut, or added separately, such as by welding or adhesives, to support the intermediary suture 5M. The addition of a mid-line or mid-waist suture 5M to the middle cylinder B also adds to the integrity and radial strength of the longer A stent module (a three stent module, A-B-C, is preferred). The intermediary loops 15M formed in each strut are preferably formed by the stent wires with the intermediary loop 15M formed with the loop aligned on the axis of the cylinder (parallel with the strut) but outwardly extending from the outer surface of the cylinder, e.g., perpendicular to the outer surface or the stent perimeter, as shown in FIGS. 5B and 5B-1. Such a loop provides an intermediary hinge point for the associated strut 14, allowing the strut 14 to fold radially outward at the hinge point of the loop 15M. This is contrary to the top loops 15, which are formed to be contained on the surface of the stent cylinder, e.g., tangential to the sent perimeter. See FIG. 5A-1. The top loops 15 are on the surface of the stent cylinder.

Figure 8:
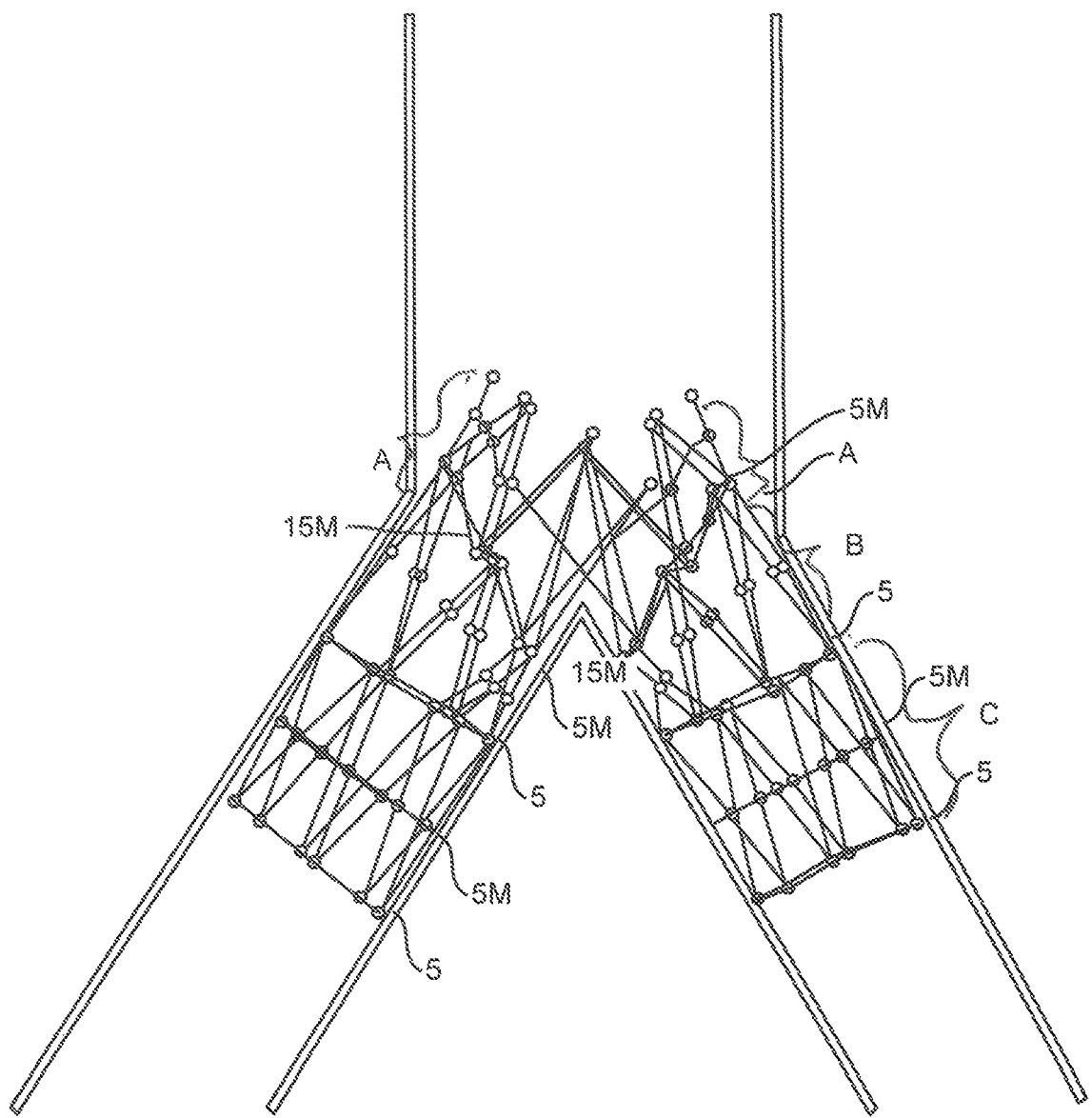
FIG. 8 is a cross sectional view though the iliac vein near the vena cava showing a bilateral deployment of two angled Z stent modules in the two confluence common iliac veins.

The original prior art modular design used in the iliac vein incorporated sutures at both the upper and lower terminating ends of each stent in the modules. The proposed modification eliminates the uppermost suture, in the topmost cylinder A, and adds a suture 5M preferably about 1.25 cm below the top loops 15 of the upper end of the struts 14 in the first cylinder. The suture 5M will pass through intermediary loops 15M on the struts of the uppermost cylinder A. These intermediary loops can be simple loops or more preferably spring loaded by forming the wire forming the stent into loops 15M in the struts 14 in a direction radially outward to the stent cylinder but parallel to the axis orientation of the strut, such as shown in FIGS. 5B and 5B-1. With the topmost suture 5 eliminated, when this modified stent is inserted and deployed so that the intermediary loops 15M of the topmost cylinder A are positioned just within the vena cava, the topmost cylinder A struts will have some tendency to splay out. The top half of the struts 14 in cylinder A will hinge radially outward, from the spring action of the middle loops 5M, unrestrained by the uppermost suture, allowing that portion of the topmost Z stent A in the vena cava to partially unfold or hinge outwardly towards the wall of the vena cava. This allows the unrestrained topmost section A of the "Z" in a bilateral configuration (e.g. one deployed in the left and another deployed in the right common iliac veins) to fully extend almost 1.25-1.5 cm into the vena cava without jailing, by allowing the terminating ends of the two topmost stents to lay almost flat or partially unfold (if the intermediary loops 15M are not within the vena cava) and avoid substantial interference with one another by interdigitating the top ends of the exposed portion of the struts 14 within the vena cava. See FIG. 8. When bilateral stents are deployed in a single stage or two stage procedure, and properly orientated, the upper end of each topmost stent cylinder A is positioned in the vena cava and are not suture-restrained by a top suture, allowing almost 1.5 cm of cylinder A to extend into the vena cava before interference or obstruction or restriction by the middle suture 5M occurs. The net effect is to reduce the combined width of the two stents at the upper end in the vena cava, as the interdigitated ends present in the vena cava are similar to the footprint of a single Z stent. Preferably, the bottommost stent C in this modification also removes the sutures from the terminating end of the bottom most cylinder C to avoid a modular stent that has an orientation. See FIG. 5.

Second Preferred Embodiment—Beveled Upper End

Figure 7:
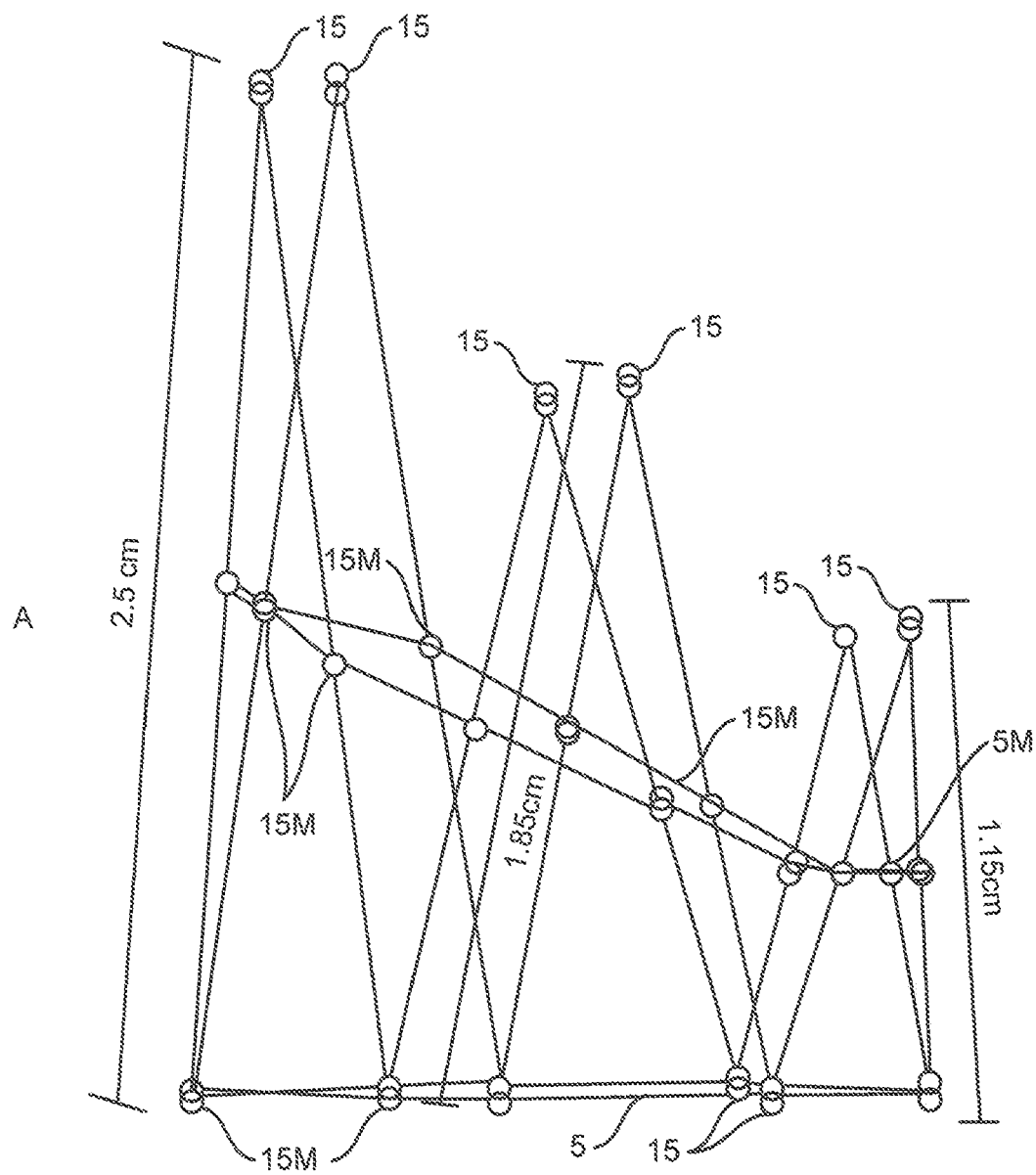
FIG. 7 is a side elevation view of the top of an angled Z stent showing the intermediary loops positioned parallel with the angled top loops or eyelets.
Figure 9:
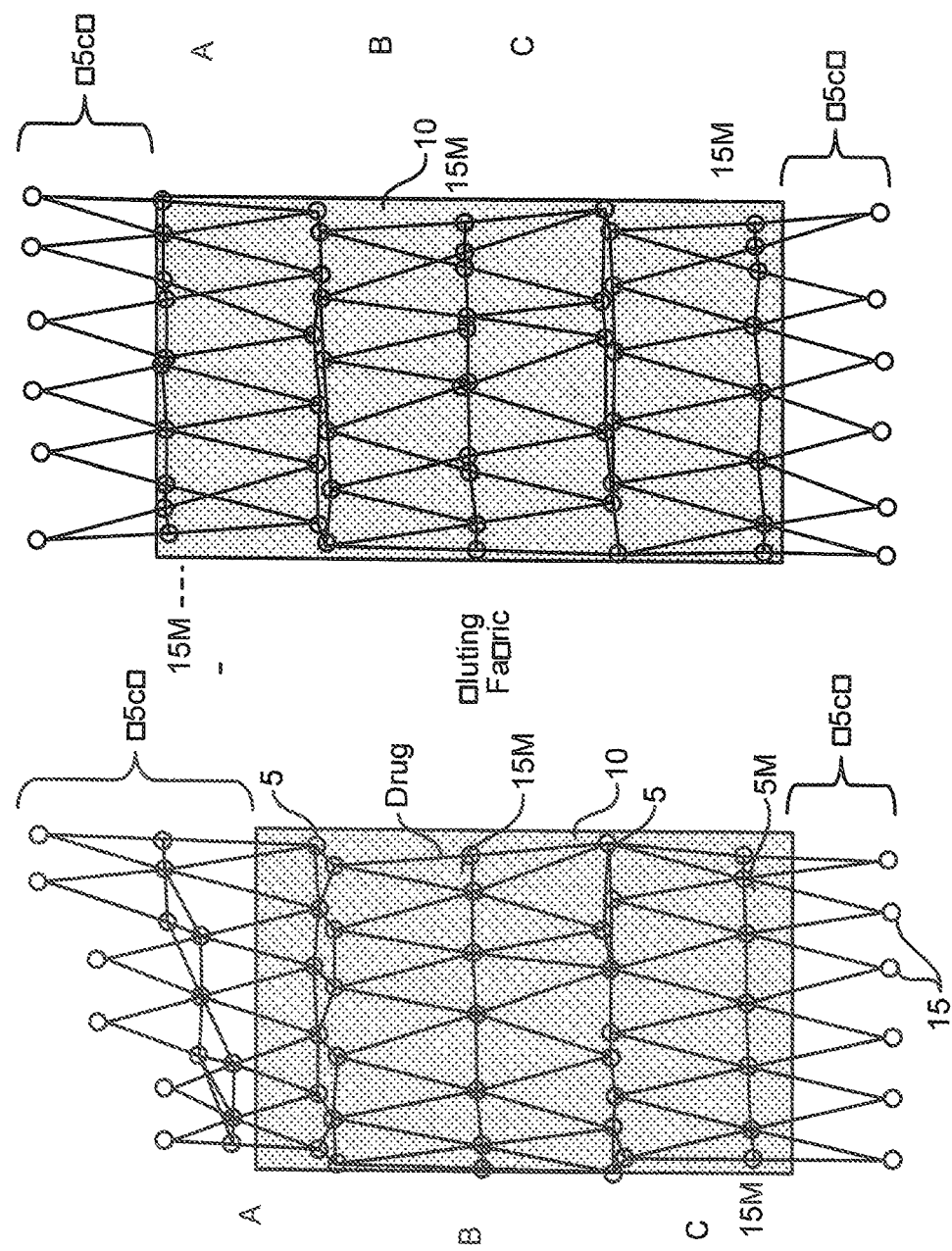
FIG. 9 is a side view of a deployed three stacked Z stent module with intermediary loops having a drug eluting fabric sheath positioned on the exterior of the module.

A second embodiment is to have the upper topmost cylinder A struts positioned to produce a beveled top surface, where the beveled angle is preferably an angle similar or slightly less than that of the angle of join of the two common iliac veins (approximately 28-40 degrees). As a consequence, with two such stents in place, each with a top suture, one in each common iliac vein, and both extending into the vena cava about 1.5 cm, if the two angled top ends face one another, the two stents will almost meet in in the vena cava and approximate a single U or V shaped stent (see FIG. 8). For a six strut cylinder embodiment (three per side) with a deployed diameter of 2.5 cm, the height of each semi-cylinder consisting of three struts will vary; each strut will gradually decline in length from 2.5 cm to 1.85 cm to 1.15 cm as shown in FIG. 7). The net result is that the upper mouth of the topmost stent cylinder A will be sloped or beveled preferably by about 28-40+ degrees. Together, the right and left stents would more closely approximate a single U or V shaped stent, with the angle of the U or V is about 28-40+ degrees. See FIG. 9.

Because of the bevel, meshing or interdigitating of the ends of the bevel may not be necessary as the composite diameter of the two stents, when deployed with the beveled ends facing each other, may not exceed desirable limits. Optionally, an intermediary suture 5M (and intermediary loops) may be included near the top of the beveled stent and follow the bevel or slopes down greater than the bevel, to assist interdigitating of the ends of the struts in a bi-lateral deployment. This intermediary suture may be eliminated if a suture 5 located at the beveled end would prevent intermingling of the struts. The intermediary suture 5M, can be located near the beveled ends or below; for instance, 0.5 cm below the ends of the struts forming the bevel. If the bevel in the cylinder walls is constructed with struts of declining heights, the intermediary suture 5M can be mounted about 0.1 cm from the top of the tallest strut and sloping down to 0.5 cm from the top of the shortest strut through simple intermediary loops 15M in the struts as described above. See FIG. 9. The upper 0.5 cm of the struts 14 will be free to mesh with a contralateral stent to a limited extent. Additionally, the bevel design will minimize chances of jailing the opposite iliac vein. Proper placement can be done if each strut bevel is marked (such as by gold plating) to be visible during placement. As the stent is extruded from the containing sheath during deployment, it can be rotated to place the stent in this proper orientation under fluoroscopy. A single beveled stent may be used with an unbeveled stent and also achieve interdigitation, but not to the extent archived from using two beveled stents.

Differential Suture Constraint

In the present V or U design, when all struts 14 are fully constrained by a bevel following suture, 5M or 5B, the deployed beveled stents A together form a U or V shaped cylinder of substantially uniform diameter in the vena cava. By using less constraint, for instance by placing the topmost suture closer to a mid-waist suture 5M (by adding intermediary loops 15M on the mid points of the struts), the resulting stent A will flare when deployed. The lower end of the cylinder C can also be flared and beveled as desired to avoid an orientated modular stent (that is, either end can be used in the vena cava).

Differential constraint can also be used to produce a tapered stent (FIG. 6C), or a stent flared at the upper end (FIG. 6A), or an hourglass shaped stent (FIG. 6B). FIG. 6 shows a single stent embodiment, but the techniques can be expanded to stacked modular designs. This is accomplished by varying the length of the various sutures 5, 5M in the upper and lower ends of a single Z stent embodiment (or upper and lower cylinders in a modular stent), and the intermediary sutures (or sutures joining the cylinders in a modular stent) can also be varied in length to produce the desired shape. With a flared stent (FIG. 6A) the stent ends facing the direction of blood flow out of the stent (i.e., the ends closest to the heart), will be flared by using a longer suture at the flared end, to help prevent distal migration of the stent, a potential problem at the confluence. Additionally, a flared stent at the upper ends will allow extension of the stent particularly in the caudal direction, consistent with the flare needed. For a tapered stent (FIG. 6C) with the taper growing upwardly, the uppermost suture is the longest and the lowermost suture is the shortest, the suture lengths can be varied in length as an application of the Poiseuille equation, to attempt to maintain constant flow through the stent, as explained in the unitary stent described in U.S. patent application Ser. No. 17/444,558 to Raju, hereby incorporated by reference. In this application, the flare or taper is designed to maintain the ratio of [(radius at point P)$^4$/(stent length at to a point P] as constant.

The stent diameters used above are exemplary, as well as stent lengths, and are not limiting. Stent diameters smaller than the stents described above can be used for caudal stent extensions in most any iliac vein segment, where the stent ends are preferably fixed according to U.S. patent application Ser. No. 14/665,603 to Raju and in Raju, et al., *Optimal Sizing of Iliac Vein Stents. Phlebology*, V33 2018, both incorporated by reference.

Flared upper stent ends will result in closer apposition at stent overlaps of different diameter stents and prevent 'shelving' at stent joints. The desired degree of flaring can be controlled by using differential suture constraint (e.g., different length sutures). For use in the iliac system, a 4 mm flaring over a basic cylinder diameter (2.5 cm in length) is suggested.

Tapered Stent

Differential suture constraint can also be used to produce a tapered stent, for use in the iliac system where a reverse taper is desired. The same stent can be used in almost any position in the iliac vein system by varying the length of the sutures to obtain the desired cylindrical tapered structure preferably with suture diameter as taught in U.S. patent application Ser. No. 14/665,603 to Raju and in Raju, et al., Optimal Sizing of *Iliac Vein Stents. Phlebology* V33, 2018. Additionally, flared stents can be manufactured and used in the venous systems, as taught in Unitary Stent and Balloons, U.S. patent application Ser. No. 17/444,558 (hereby incorporated by reference). Specific sizing is preferred for use of stents in the iliac-femoral vein segments for optimal sizing, as described in U.S. patent application Ser. No. 14/665,603 to Raju and in Raju, et al., *Optimal Sizing of Iliac Vein Stents. Phlebology* V33, 2018, all incorporated by reference.

Drug Eluting Z Stent

A common complication of iliac vein stenting is the development of in-stent restenosis (ISR) that reduces the functional efficiency of the stent. Early ISR may be due to thrombus lining of the stent. Mature ISR has considerable fibrin content. The proposed modifications can incorporate a fabric or other thin sheet made from material to which heparin or other agents imbedded or infused in the material would inhibit thrombus formation. Anti-fibrotic agents such as paclitaxel or others can be bonded as well to reduce ISR formation. The fabric 10 will cover the outside of the stent like a pillowcase and will contact the vein wall. Preferably, only the "body" of the modular stent (between the two outermost sutures) will be covered, leaving the upper and lower ends (preferably about 2.5 cm) exposed for inflow from tributaries (e.g., hypogastric vein) or the opposite iliac vein. Also, the absence of fabric near the ends will facilitate better apposition at stent joints. The fabric can be sized for the sprung diameter of the stent or be an elastomeric fabric, expandable to the stent deployed diameter.

Combinations

The above modifications (beveled, or free upper end) can be combined or engineered alone or used in conjunction with shape formed stent modules. The drug eluting material can also be combined with any of the modifications/combinations described.

Caliber

The optimal caliber for common iliac vein stents is 18-20 mm, for external iliac vein 14-16 mm, and for common femoral vein is 12-14 mm. It is suggested that the modified Z stent is made with the following calibers in the deployed state (diameters in mm): 10, 12, 14, 16, 18, 20, 25, 22, 24, and 26 mm. A size slightly larger than a native vein should be chosen. This will generally correspond to the optimal caliber for the various vein segments described above. If the size is properly chosen, good hemodynamic performance and minimization of stent migration/embolization can be expected.

Length

The original prior art design was specified as 5 cm in length which has potential to embolize or migrate. The proposed three stacked cylinder design (or using two Z stents in a two stack embodiment, or a single cylindrical embodiment) id designed to increase the length of each strut to achieve a 7.5 cm modular stent length in 14 mm or larger caliber sizes. Chances of embolization or migration will be mitigated by a larger surface contact of the stent with the vein wall. The modified Z stent preferably can be made in the following lengths matched with calibers: 7.5 cm lengths for caliber (diameter) 14 mm and larger; 4 and 6 cm length for caliber (diameter) less than 14 mm. The Z stent marketed design discussed above incorporated two or three cylinders, each 2.5 cm long. This allows the stent to bend at the joint between two cylinders. We propose that at least three cylinders preferably be the minimum for all proposed lengths. This is optional but preferred.

Gradually expanding stent caliber, as taught in U.S. patent application Ser. No. 17/444,558 to Raju can easily be accommodated in the modified Z stent embodiments simply by altering the lengths of the sutures as needed to achieve the desired stent taper.

Special Delivery Capsule

Figure 10:
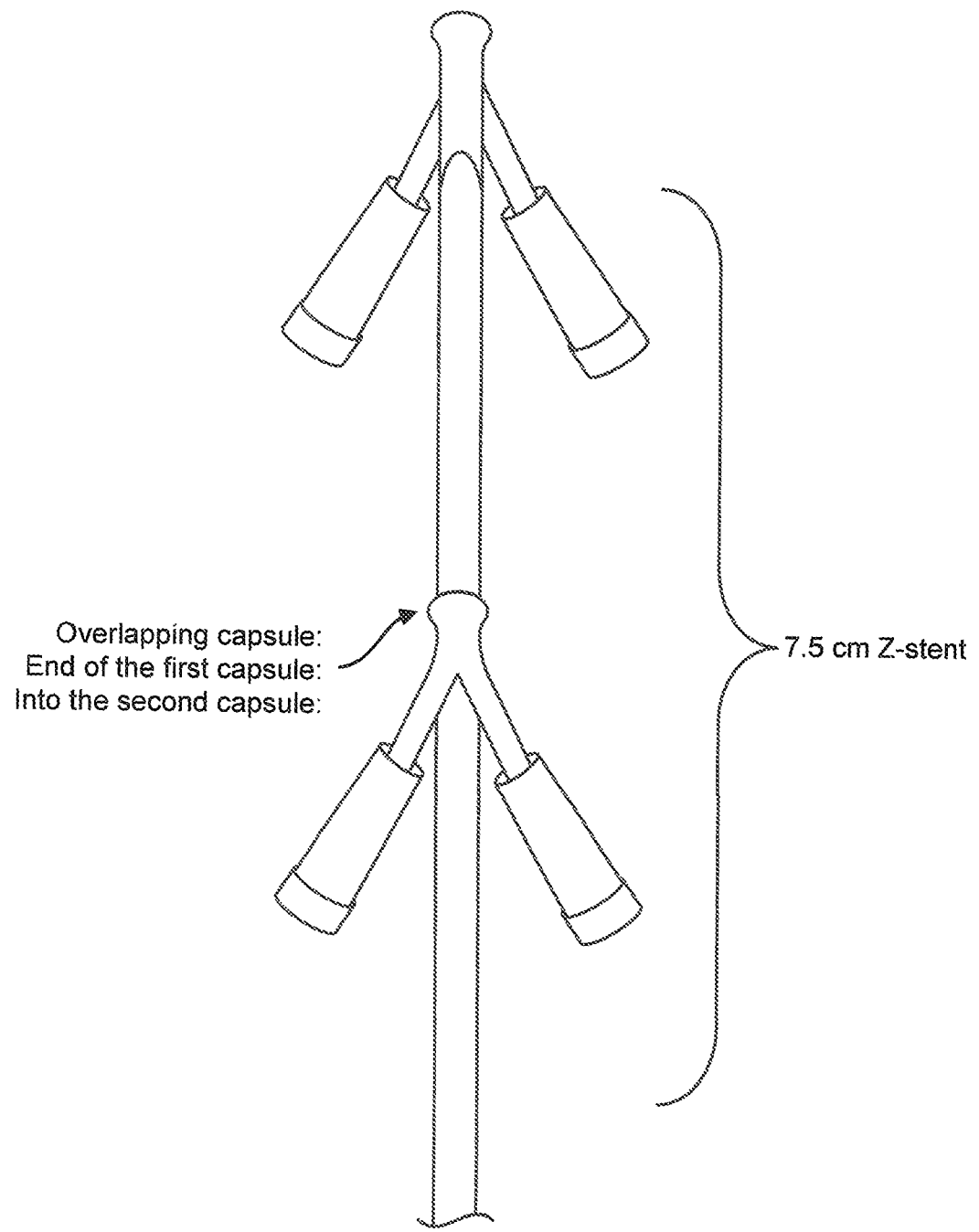
FIG. 10 is a top view of a device for deploying a stacked stent module.

The original Z stent came in a 6 cm "peel away" capsule that could be loaded into the delivery sheath after peeling it away. We propose a telescoping two capsule version 8.5 cm long for the 7.5 cm length stents. The bottom capsule is unloaded first to deploy the lower end of the stent into the delivery sheath. Then the top capsule is peeled away pushing the top portion of the stent into the delivery sheath. See FIG. 10.

As can be seen, the above modified Z stent and Z stent modules are adaptable to most applications in the iliac vein system, they resist migration and can provide for optimal flow characteristics through the stented system.

The invention claimed is:

1. A Z stent comprising a metal alloy wire formed in a zigzag pattern into a closed cylinder having a central lumen, the zigzag pattern resulting in a series of Z shaped forms, each Z shaped form comprising three wire struts, the cylinder having a top end formed by a top end of the struts, and a bottom end formed by a bottom end of each strut, the bottom end of each strut terminating in a bottom loop, an intermediary loop positioned on each strut between the top end and bottom end of the associated strut, each intermediary loop formed by the alloy wire into a spring loaded loop, a closed intermediary suture extending though each said intermediary loops, encircling the Z stent cylinder.

2. A Z stent comprising a metal alloy wire formed in a zigzag pattern into a closed cylinder having a central lumen, the zigzag pattern resulting in a series of Z shaped forms each Z form comprising three wire struts, the cylinder having a top end formed by a top end of the struts, and a bottom end formed by a bottom end of each strut, the top end of each strut terminating in a top loop, the bottom end of each strut terminating in a bottom loop, the top end of the cylinder forming a single angled or beveled surface, a closed top suture passing through the top loops, and a closed bottom suture passing through the bottom loops.

3. The Z stent as in claim 1 where the intermediary loops are positioned a set distance below each top end of each associated strut.

4. The Z stent of claim 3 wherein each intermediary loop is located about 1.25 cm below the top end on the associated strut.

5. A series of Z stents stacked one on top of another to create a stent module, each Z stent in said series comprising a metal alloy wire formed in a zigzag pattern into a closed cylinder having a central lumen, the zigzag pattern resulting in a series of Z shaped forms, each Z form comprising three wire struts, the cylinder having a top end formed by a top end of the struts, and a bottom end formed by a bottom end of each strut, the top end of each strut is terminated in a top loop, the bottom end of each strut is terminated in a bottom loop, where, in a pair of adjacent Z stents in the stack, one upper Z stent and one lower Z stent are connected by a joining suture passing though the upper Z stents bottom loops and the lower Z stents top loops, whereby the top end of an upper most Z stent in the stack is formed at a single angle of about 10-20 degrees with respect to the bottom end of the uppermost Z stent, each top loop in the uppermost Z stent is further connected by a closed suture positioned through its top loops.

6. The Z stent as in claim 1, where the intermediary loops are positioned a set distance below each top loop on an associated strut loop.

7. A Z stent comprising a metal alloy wire formed in a zigzag pattern into a closed cylinder having a central lumen, the zigzag pattern resulting in a series of Z shaped forms, each Z form comprising three wire struts, the cylinder having a top end formed by a top end of the struts, and a bottom end formed by a bottom end of each strut, the top end of each strut terminated in a top loop, the bottom end of each strut terminating in a bottom loop, an intermediary loop positioned on each strut between the top end and bottom ends of the associated strut, each intermediary loop formed by the alloy wire into a spring loaded loop, each intermediary loop forming a hinge point for the associated strut, a closed intermediary suture extending though each said intermediary loops, a closed top suture passing through the top loops, and a closed bottom suture extending through the bottom loops, where the intermediary suture, the bottom suture and the top suture are not all the same length.

8. A Z stent according to claim 7 where the top suture is longer than the bottom suture.

9. A Z stent according to claim 7, where the top suture is longer than the intermediary suture, and the intermediary suture and bottom suture are the same length.

10. A method of use of a pair of modular Z stents, where each modular stent comprises a series of Z stents stacked one on top of another, each Z stent in said series comprising a metal alloy wire formed in a zigzag pattern into a closed cylinder having a central lumen, the zigzag pattern resulting in a Z shaped forms each Z form comprising three wire struts, each cylinder having a top end formed by a top end of the struts in each respective cylinder, and a bottom end formed by a bottom end of the struts in each respective cylinder, the top end of each strut is terminated in a top loop, the bottom end of each strut is terminated in a bottom loop, whereby the top end of an uppermost Z stent in the stack is formed at a single angle or bevel of about 28-40 degrees with respect to the bottom end of an uppermost Z stent, each top loop in the uppermost Z stent is further connected by a closed suture positioned through the top loops; where for each pair of adjacent Z stents in the stack, one upper Z stent and one lower Z stent in the stack are connected by a joining suture passing though the upper stent's bottom loops, and the lower stents top loops where the first modular Z stent is deployed in a first common iliac veins of a patient and positioned so that the uppermost Z stent in the first modular Z stent is partially located in the first common iliac vien with the top end extending into the vena cava about 1.25-1.5 cm, and the first modular Z stent is further positioned in the first common iliac vein so that the angled top surface of the uppermost Z stent in the first modular Z stent is facing a second common iliac vein;

the second modular Z stent being deployed in the second common iliac vein of the patient and positioned so that the uppermost Z stent of the second modular Z stent is partially located in the second common iliac vein with the top end extending into the vena cava about 1.25-1.5 cm, and the modular Z stent is positioned so that the angled top of uppermost Z stent in the second modular Z stent is facing the first common iliac vein; and whereby the two modular Z stents approximate a single V or U shaped stent, each uppermost Z stent further comprises an upper closed positioned through the top loops fo the respective uppermost Z stent.

11. A method of placing two modular Z tents in the iliac vein system of a patient, where each modular Z stent comprises a series of Z stents stacked one on top of another, each Z stent in said series comprising a metal alloy wire formed in a zigzag pattern into a closed cylinder having a central lumen, the zigzag pattern resulting in a series of Z shaped forms, each Z shaped form comprising three wire struts, each cylinder having a top end formed by the a top end of the struts in the repsective cylinder, and a bottom end formed by a bottom end of each strut in the respective cylinder, an intermediary loop positioned on each strut between the top end and bottom end of the associated strut on at least an uppermost Z stent cylinder, each intermediary loop formed by the alloy wire into a spring loaded loop, each intermediary loop forming an outwardly directed hinge point for the associated strut;

a closed intermediary suture extending though each said intermediary loops on the respective Z cylinder, encircling the associated Z stent cylinder;

for each pair of adjacent Z stents in the stack, one upper Z stent and one lower Z stent, where the bottom end of each strut in the upper Z stent has a bottom loop, and the top end of the lower Z stent has a top loop formed on each strut, where the adjacent Z stents in the stack are connected by a joining suture passing though the upper Z stent's bottom loops and the lower Z stent's top loops, when the first modular Z stent is deployed in a first common iliac veins of a patient and positioned so that an uppermost Z stent in the first modular Z stent is located partially in the the first common iliace veins and the top end of the uppermost Z stent extending into the vena cava;

and the second modular Z stent is located in the second common iliac vein and positioned so that the top end of an uppermost Z stent of the second modular Z stent extends into the vena cava.

12. The Z stent of claim 1 where the intermediary loops are formed by the alloy wire so that the intermediary loop is inline with the strut but extends outwardly from an exterior surface of the stent cylinder.

13. The Z stent of claim 1 where the top loops and bottom loops are formed by the alloy wire, so that the top loops and bottom loops are formed tangential to an exterior surface of the associated stent cylinder.

14. The Z stent of claim 1 where the sutures are formed from a plastic material or a metal alloy material.

\* \* \* \* \*